United States Patent [19]

Johnson

[11] 4,151,809

[45] May 1, 1979

[54] SYSTEM FOR EVENLY APPLYING LIQUID TO A SURFACE

[75] Inventor: Leighton C. Johnson, Edwardsburg, Mich.

[73] Assignee: Miles Laboratories, Inc., Elkhart, Ind.

[21] Appl. No.: 826,759

[22] Filed: Aug. 22, 1977

Related U.S. Application Data

[63] Continuation of Ser. No. 730,864, Oct. 8, 1976, abandoned.

[51] Int. Cl.² .................... B05C 5/02; B05C 11/02
[52] U.S. Cl. ................................ 118/6; 118/401; 427/2
[58] Field of Search .............. 118/2, 6, 7, 8, 400, 118/401, 506, 407, 412; 427/2, 4; 141/180; 198/341, 339

[56] References Cited

U.S. PATENT DOCUMENTS

| | | | |
|---|---|---|---|
| 2,599,478 | 6/1952 | Peters et al. | 118/6 X |
| 2,986,114 | 5/1961 | Fuchs et al. | 118/6 X |
| 3,431,886 | 3/1969 | McCormick et al. | 118/401 X |
| 3,908,584 | 9/1975 | Rague | 118/6 X |
| 4,060,052 | 11/1977 | Algeri et al. | 118/2 |

FOREIGN PATENT DOCUMENTS

1203213  8/1970  United Kingdom .................. 118/19

Primary Examiner—Morris Kaplan
Attorney, Agent, or Firm—Roger N. Coe

[57] ABSTRACT

Apparatus and the method of operation thereof are described for conveying an object, such as a microscopic slide, over a flat liquid-applying surface and interrupting the advance of the object for a predetermined time period while the object is at rest in position of the liquid-applying surface to achieve even application of a treating liquid to the object. The treating liquid can be injected into the space between the object and said flat liquid-applying surface while the object is substantially stationary or prior to interruption of the object movement.

6 Claims, 6 Drawing Figures

SYSTEM FOR EVENLY APPLYING LIQUID TO A SURFACE

This is a continuation of application Ser. No. 730,864, filed Oct. 8, 1976, abandoned.

FIELD OF THE INVENTION

The present invention relates to a system for applying liquid to at least one surface of an object and, more particularly, to an improved system for rapidly and evenly applying liquid to one surface of a microscopic slide. Still more particularly, the invention relates to an improved system for rapidly and evenly staining a plurality of seriate microscopic slides.

BACKGROUND OF THE INVENTION

For purposes of microscopic examination of certain material, particularly cellular materials such as blood, tissue and the like, it is customary to place a smear of a liquid or substrate containing the material (e.g., a smear of plasma containing blood cells), or a thin section of the material itself (e.g., a thin slice of animal or plant tissue) on a transparent plate or slide. Thereafter, the material is stained by subjecting it to contact with solutions which stain or dye only certain constituents of the material or cells and this provides a contrast which facilitates visual examination.

Various staining procedures are utilized to produce different effects. For example, a solution can be employed to color a transparent substrate and thus provide contrast to essentially colorless cells; other solutions can be utilized to effect color differences between various parts of the cell. Solutions can be used to stain only portions of a cell, e.g., the nuclei and not the cytoplasm. In a procedure known as negative staining the cells can be caused to appear colorless against a colored background. Certain procedures are relatively simple and require the use of only a few solutions. Others, however, are complex and require successive applications of relatively large numbers of solutions.

In many of these staining procedures, certain of the solutions merely prepare or fix the substrate whereas the actual stains are made by one or more natural or synthetic dyes. The dyes selected are, of course, suited for the type of cell and the staining desired. The oxazine dyes, the triphenylmethane dyes and the thiazine dyes are examples of some families of dyes that are commonly used.

In a conventional staining procedure it has been the general practice to dip the slide successively into a series of containers holding different solutions, the slide being allowed to remain in each solution for a predetermined time interval of perhaps several minutes before removing and dipping the slide into a succeeding solution. Usually the last container holds a wash, such as water, after which the slide is dried for examination. These operations can be performed manually by a technician or in automated equipment which has been developed for such operations.

Depending upon the nature of the material being stained and the type of staining desired, as many as twelve solutions are sometimes required in the overall procedure. The fact that many slides are frequently involved merely multiples the problems. Furthermore, when successive slides are passed through the same container of solution, as in the case where dipping is employed, there is a danger of contamination of the solution. The danger increases when the same solution is used in different staining procedures for different types of materials and substrates.

In another system microscopic slides are stained by dripping stain onto the surface of a slide. Buffer is then added and an air jet is used to mix the buffer and stain on the surface of the slide. Obviously, very careful regulation of the air jet is essential in order to obtain an even distribution and mixing of buffer and stain.

In U.S. Pat. No. 3,431,886 apparatus is described for automatically applying a single liquid or multiple liquids to the bottom face of a generally horizontally disposed slide while the slide is being conveyed in spaced relation over and generally parallel with a flat liquid-applying surface. The HEMA-TEK ® apparatus described in the patent and sold by Miles Laboratories, Inc. of Elkhart, Ind. has now become an industry standard for applying one or more liquids to a slide. The apparatus and system for applying liquids disclosed in U.S. Pat. No. 3,431,886 is hereby incorporated by reference.

For certain purposes, however, even further control of the application of liquids to slides has been desired in order to achieve a greater degree of control of liquid stain intensity and uniformity of application. It has also been desired to increase the speed at which slides are stained by automated equipment.

SUMMARY OF THE INVENTION

An object of the present invention is to provide an improved apparatus and system for treating one surface of a generally flat object with liquid.

Another object of the present invention is to provide an improved apparatus and system for automatically and successively applying liquid stain to materials carried on a plurality of slides.

Still another object of the present invention is to provide an improved apparatus for automatically staining material carried on a slide by successively effecting contact between such material and each of a plurality of solutions in such a manner as to achieve rapid and even staining of said material.

A further object of the present invention is to provide an improved apparatus for controlling the degree of stain intensity and cellular differentiation of microscopic slides.

Yet another object of the present invention is to provide an improved apparatus for automatically staining material carried by a plurality of slides which will provide increased instrument output.

Yet another object of the present invention is to provide an improved control system for controlling the operation of slide staining apparatus.

In accordance with the present invention apparatus is described for conveying seriate, flat-surfaced objects, such as microscopic slides, along a predetermined path over a flat liquid-applying surface, injecting treating liquid into the space between an object and the flat liquid-applying surface at a time when the object is moving into position or is in position over the liquid-applying station, and temporarily interrupting the advance of the object while the latter is in position over the liquid-applying station. While in this position liquid is applied to the object. After a predetermined period of time following application of liquid (e.g. 10 seconds to one minute), movement of the object along the predetermined path is resumed. The described interruption of movement of the objects and conveying of the objects from station to station (location to location) provides an even application of liquid over the surface, as described hereinafter, of the objects and permits increased instrument output compared with the now standardized procedure of applying liquid to slides or other flat objects while they are continuously moved across a flat liquid applying surface.

BRIEF DESCRIPTION OF THE DRAWINGS

Other and further objects, advantages and features of the invention will be apparent to those skilled in the art from the following detailed description thereof, taken in conjunction with the accompanying drawings in which.

DESCRIPTION OF THE PREFERRED EMBODIMENTS

Figure 1:
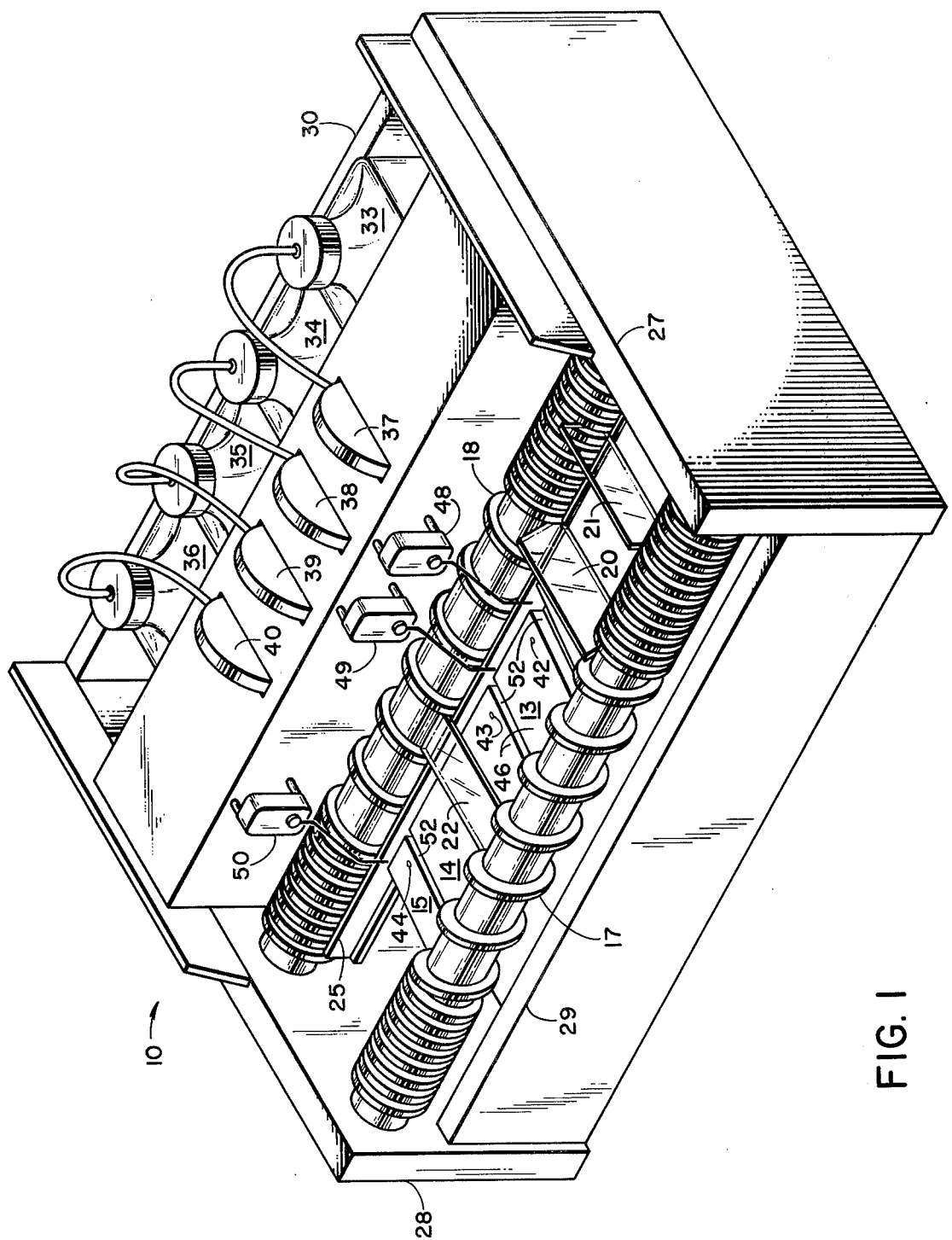
FIG. 1 is a perspective view of the apparatus of the present invention showing a helical feed mechanism for conveying slides along a platen.

Very generally, the present invention relates to apparatus for automatically applying a single liquid solution or multiple liquid solutions to at least one face or surface of a flat-surfaced object. The system is particularly useful for automatically staining material carried on one face of each of a plurality of seriate microscopic slides. In the embodiment illustrated in FIG. 1, slide staining apparatus (10) is provided which comprises a plurality of treating, ie., liquid-applying, stations (13), (14) and (15) and conveyor elements comprising helical conveyor elements (17) and (18) for advancing generally flat objects, such as transparent glass slides (20), (21) and (22), past said plurality of treating stations. A liquid-applying device located at each of the stations automatically subjects one face of each slide to contact with the metered quantity of desired liquid.

To provide a compact apparatus capable of handling a fairly large number of slides, the feed mechanism is designed to accept slides, such as slide (20), aligned in generally parallel face-to-face relationship with each slide disposed so as to rest upon a longitudinal edge and thereby lie in generally vertical planes. As the slides are advanced by the feed mechanism they are tilted forward, such as slide (21), so as to eventually lie flat and be aligned in generally parallel edge to edge relationship in a generally horizontal plane, such as slide (22), as they pass over the liquid-applying stations. After these slides have passed liquid-applying stations (13 and 14) they are washed at station (15) and then automatically removed from the feed mechanism.

Now referring more particularly to the drawings, slide staining apparatus (10) includes a pair of end plates (27) and (28), front plate (29) and a back plate (30). For convenience, slide staining apparatus (10) has been shown with the top covers removed in order to show various operative components of the apparatus.

The feed mechanism includes a generally horizontal track which extends longitudinally of the apparatus and is defined by a pair of generally parallel rails (25), only one of which is shown in FIG. 1, each adjacent and generally parallel with one of the helical conveyor elements (17) and (18). The rails (25) are spaced apart horizontally a distance less than the length of a standard glass slide. Conventionally, a glass slide is about three inches in length and one inch in width. Rails (25) can be formed from separate bars or rods or from the same "U" or "I" shaped channel member. In a standard operation of this type of apparatus, the slides straddle or span rails (25) with each rail engaging each slide at a point spaced inwardly from an end thereof.

In the preferred feed mechanism illustrated in FIG. 1 slides are advanced along rails (25) in such a way as to maintain a predetermined spacial relationship between the slides. In this embodiment the conveyor mechanism includes generally helical conveyor elements (17) and (18) which flank rails (25) and can be rotated by a drive motor, such as the motor shown in FIG. 6. The motor rotates conveyor elements (17) and (18) in opposite directions and thereby moves objects, such as glass slides, along a predetermined path defined by the track. The conveyor elements are preferably substantially identical except for the direction of their helical configuration. The pitches of the helices which form conveyor elements (17) and (18) can vary along the length of the conveyor elements. At the right hand end of the conveyor elements, as seen in FIG. 1, the pitches of the conveyor elements are such that the turns of the helices are quite close together. The gap between adjacent turns of a given helix being only slightly greater than the thickness of the flat object to be treated, for example, a glass slide. The pitches of the helices in their intermediate portions change so that the gap between adjacent turns is enlarged to a distance slightly greater than the width of the flat object to be treated. These changes in pitch of each of the helices enable the slides to be rotated from a generally vertical position (normal to the place of the tract) to a generally horizontal position (parallel to the plane of the tract). Because the helices of conveyor elements (17) and (18) are designed principally for use with glass slides, they are preferably made from a material which withstands wear against glass, such as chrome plated stainless steel, a hard coated aluminum such as NITUF ® and the like. Hard coatings are prepared using high current densities and low temperature electrolytes to produce finishes of greater thickness and density than conventional anodic coatings. Commercially these hard coatings are also known as "Alumilite" hard coatings, "Martin" hard coatings, "Sanford" or "Hardes".

The outer and inner diameters of helical conveyor elements (17) and (18) are such that the minimum distance between the conveyors is less than the length of a standard slide. Thus, slide (22), for example, is moved or transported along rails (25) between adjacent turns of the helical portions of conveyor elements (17) and (18). The helical conveyor elements can be rotated by the same drive motor using a series of gears (not shown) causing simultaneous, but opposite, rotation of said elements. Thus, the conveyor elements (17) and (18) are rotated in opposite directions, one element (18) being rotated in a counterclockwise direction, and the other element (17) being rotated in a clockwise direction, as viewed in FIG. 1. Accordingly, since one helical conveyor element is left handed and the other is right handed the rotation of these helical elements causes slides to advance from the right to the left across the apparatus.

It will be understood that instead of a gear drive the helical conveyor elements can be driven by a chain drive. It will also be understood that, if desired, two right-handed helices or two left-handed helices could be used by modification of the drive so that both helices would be turning in the same direction.

The slides are advanced to the left past the various liquid-applying stations incident to the rotation of the helical conveyor elements (17) and (18). When microscopic slides are handled in the illustrated apparatus the material to be stained is carried by the lower face of the slides when the latter travel in the horizontal position past the liquid-applying stations. Two separate liquid-applying stations (13) and (14) and one wash station (15) are illustrated in the drawing. However, it will be understood that any number of stations can be provided and that the number showing is only illustrative of a particular staining procedure for staining blood smears. In carrying out the Wright procedure in the apparatus, the staining liquid is applied at the first station, a buffer liquid mixed with stain by suitable means, such as a mixing coil (not shown), is immediately applied at the second station and a washing liquid is applied at the third station. The liquid is supplied from containers (33–36), pumped through suitable pumping means, e.g., peristalic pumps (37–40), and injected up through orifices (42–44) in platen (46). Suitable timing means such as soft action switches (48–50), activated by trip wires and movement of slides, can be used to activate the pumping means. One suitable switch is switch number 268-0200-00 made by the Robertshaw Company of Columbus, Ohio.

Each of the liquid-applying stations, exemplified by station (13), includes a flat liquid-applying upper surface portion of a stationary platen (46), securely mounted within the recess portion between rails (25). The platen is positioned so that the liquid-applying surfaces thereof at stations (13), (14) and (15) are parallel with and closely adjacent to the plane of the upper surface of rails (25) so as to be parallel with and in close proximity to the lower face of a slide (22) supported by rails (25) and positioned thereover. The platen is provided at each liquid-applying station with an orifice, such as orifice (42–44), through which a predetermined quantity of liquid can be injected into the space between the liquid-applying surface of platen (46) and the overlying slide to thereby contact the lower surface of the slide and the material carried thereby with said liquid. Since the lower face of the slide is in close proximity to the liquid-applying surface, e.g., a spacing of a few thousandths of an inch (i.e., 5–12 thousandths of an inch), the surface tension of the injected liquid is sufficient to completely fill the laminar volume between the two flat surfaces and hence the lower surface area of the slide which passes in face to face relationship with the liquid-applying surface of platen (46) is thus brought into contact with the liquid.

As shown in FIG. 1, platen (46) is preferably formed from a unitary member having transverse recesses or grooves (52), which define the liquid-applying stations (13), (14) and (15).

If desired, other recess portions or grooves can be present in the platen. The purpose of such grooves is to draw liquid across the slide and/or remove excess liquid. The number, size and specific locations of such grooves will vary depending on the particular staining or liquid-applying procedures being employed. These are apparatus variations within the skill of those in the art to determine.

Figure 4:
FIG. 4 is a diagrammatical illustration of a specimen-bearing glass slide showing a gradient staining pattern which could occur with conventional automated slide-staining apparatus.

It has been found that when a slide, such as slide (22), is advanced across platen (46) by continuous motion as in prior art slide staining apparatus, a circulatory motion is set up in the liquid film between the lower face of the slide and the adjacent liquid-applying surface of the platen. This circulatory motion is caused by the fact that liquid is introduced at one side of the slide through an orifice, such as orifice (42), while the slide is moving across platen (46). Continuous movement of the slide along the track causes the treating liquid to be applied in a patterned configuration because of the surface tension and shear characteristics involved with the movement of the slide over the liquid-applying surface. A representation of a patterned configuration which can occur with the application of treating liquid under such circumstances is illustrated in FIG. 4 which shows a gradient effect produced by such liquid application. This shear or gradient effect on the slide is sometimes objectionable, particularly when the slides are to be analyzed automatically rather than being subjected to human evaluation.

Figure 5:
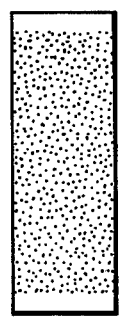
FIG. 5 is a diagrammatical illustration of a specimen-bearing glass slide showing an essentially uniform staining pattern created when the slide is stained in automated slide-staining apparatus of the present invention.

Ways have been sought to minimize the gradient effect and to permit even coverage of a slide with liquid. In addition, ways have been sought to increase the speed for advancing slides along automated slide staining equipment. Surprisingly, it has been found that intermittent motion or movement of the slides and application of the treating liquids thereto while the slides are at rest causes such liquids to be applied evenly to the slides, avoiding the shear or gradient characteristic found to be detrimental in some of the previous slide staining applications. Such application permits more rapid advance of the slides between liquid-applying stations so that the output of the instrument is increased. The time during which the slides are at rest at the liquid-applying stations following application of treating liquids can range from 10 seconds to one minute, with 30 seconds being typical when the Wright staining procedure is followed. FIG. 5 illustrates diagrammatically substantially uniform staining achieved by application of treating liquid in accordance with the present invention.

Figure 2:
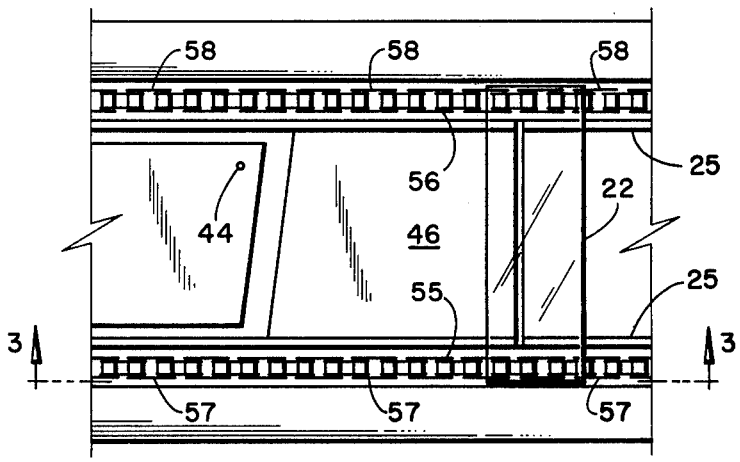
FIG. 2 is a partial top view of another feed mechanism suitable for use in accordance with the present invention.
Figure 3:
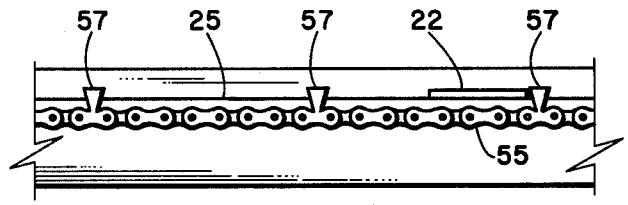
FIG. 3 is a partial side view taken along lines 3—3 in FIG. 2.

Another mechanism for conveying slides along rails (25) is illustrated in FIGS. 2 and 3. In these drawings the conveyor elements or means of FIG. 1 have been replaced by a chain drive with the upper stretches of endless link chains (55), (56) extending respectively along opposite sides of platen (46) and rails (25). Slide (22) is moved along rails (25) by tabs (57) and (58) on chains (55) and (56) which tabs extend slightly above the plane of the top of the rails to engage slide (22). Obviously, other modes or mechanisms for advancing the object to be treated can be employed.

Figure 6:
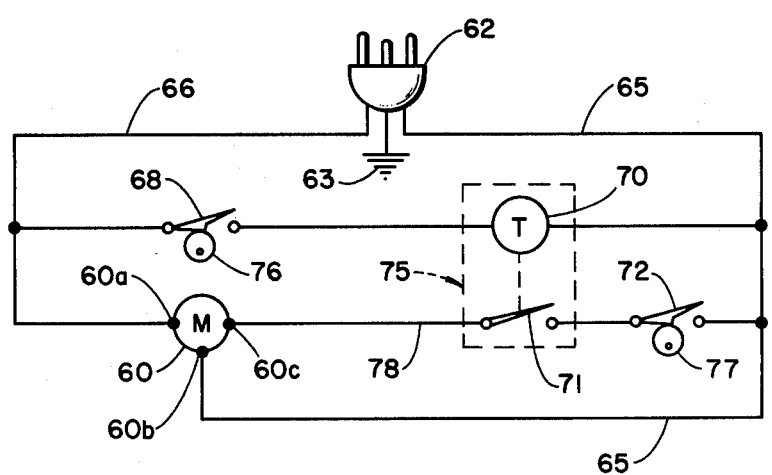
FIG. 6 is a schematic view of the electrical control circuitry for automated liquid treating apparatus in accordance with the present invention.

Referring to FIG. 6, which illustrates the electrical circuit for the apparatus, a capacitor 3-lead single phase AC motor (60) is utilized to drive the means used to convey objects over the flat liquid-applying surfaces. Motor (60) also drives cams (76) and (77) which are associated with switches (68) and (72), respectively. Motor (60) has a "hot" line terminal (60a) and separate clockwise and counterclockwise drive windings (not shown) each having one end connected to terminal (60a). The other ends of said windings are connected respectively to common line terminals (60b) and (60c) and a capacitor (not shown) is positioned across the terminals (60b) and (60c) within motor (60). Lines (65) and (66) connect terminals (60a) and (60b), respectively, to an AC source (62) which is grounded at line (63). Switches (68) and (72) are shown in FIG. 6 as being held in open position by the cams associated therewith. Operation of motor (60) rotates the cams (76) and (77) to cause closure of associated switches (68) and (72). When switch (68) closes, timer (70) of an adjustable time switch (75) having normally open contacts (71) is energized, closing contacts (71). Switch contacts (71) and (72) are connected in series into line (78) which is connected at one end to motor terminal (60c) and at the other end to line (65), so that when switch contacts (71) and (72) are both closed, power from the source (62) is supplied to both windings of motor (60), causing a dynamic braking and stopping of motor (60). The dynamic braking is thus accomplished by shunting the capacitor with the motor windings energized. One suitable motor is made by Bodine Electric Company as catalog number B8192E300M.

Stoppage of motor (60), through proper positioning of cams (76) and (77), is synchronized with arrival of the objects over the liquid-applying stations, and said objects remain at rest thereat while liquid is being applied thereto until timer (70) causes reopening of the switch (71) and release of the dynamic braking of motor (60), whereupon operation of the latter, and hence of cams (76) and (77) and of the drive mechanism for advancing objects is resumed. The cycle is repeated when the objects arrive at the next liquid-applying station and cams (76) and (77) again allow switch contacts (68) and (72) to close. A preferred time switch for use as the time switch (75) is made by the Guardian Electric Manufacturing Company of California, Inc. located in Torrance, Calif. (the timer and associated relay being model numbers 0132-1046-6100 and A410-361342-00 (12204-04)).

From the foregoing, it will be seen that this invention is well adapted to attain all of the ends and objects hereinabove set forth, together with other advantages which are obvious and inherent. The above-described apparatus and system make it possible to convey generally flat objects in a novel manner from an input station successively past one or more treating stations in a predetermined orientation and evenly treat the objects with liquid. In the illustrated form of the invention a large number of microscopic slides can be automatically and successively treated with staining liquids in a manner which achieves even staining over the surface of the slide at an ouput rate which is increased as much as from 33% to 100% (percent) over continuous movement slide staining apparatus such as that set forth in U.S. Pat. No. 3,431,886. Instead of constant relatively slow slide motion along the platen, slides are moved intermittently, but relatively rapidly, between liquid-applying stations, and liquid is applied thereto while they are substantially at rest over the liquid-applying stations. This avoids a shear fluid flow in the buffer-stain mixture applied to the slides as well as the formation of the secondary stain pattern sometimes imparted by constant travel of the slide with respect to the platen. In contrast to the prior art arrangement in which slides are moved at a constant rate while stain and buffer are applied thereto, the present invention permits greater control of stain intensity and cellular differentiation. Stain intensity is largely a function of the length of time the specimen on the slide is in contact with the stain, and this time can be readily adjusted, independent of the speed of advance of the slides between liquid-applying stations, by adjustment of this setting of time switch (75) to increase or decrease the length of time the slides are at rest over the liquid-applying stations. Intermittent slide motion, with relatively rapid movement of the slides between liquid-applying stations, contrary to what one would anticipate, results in increased output of the automatic slide staining equipment.

The present invention has all of the inherent advantages of automatic slide staining equipment. For example, it eliminates the tedious and repetitive job in which lab technicians were formerly required to prepare stained slides for microscopic examination. The invention also provides economy in staining because only a small amount, usually about one cubic centimeter of liquid, is needed for staining a slide at each station. In addition, fresh stain is used for each staining operation. Moreover, superior quality and reproducibility of results are provided because the human factor is removed, insuring uniform performance at each step.

Obviously, many modifications and variations of the invention as hereinbefore set forth can be made without departing from the spirit and scope thereof, and therefore only such limitations should be imposed as are indicated by the appended claims.

What is claimed is:

1. Apparatus for evenly applying liquid to a generally flat surface of a microscopic slide at liquid-applying stations located along a predetermined path, which apparatus comprises a track adapted for support of said microscope slide with its flat surface disposed substantially parallel to the plane of the track, means for advancing said microscope slide along said track from one liquid-applying station to another, a platen positioned in said track and having a generally flat surface disposed parallel to but spaced slightly from the flat surface of said microscope slide as it is advanced along said track over said platen, means for supplying a predetermined quantity of treating liquid onto said generally flat surface of the platen at a liquid-applying station so as to fill the space between said flat surface of the platen and the flat surface of the microscope slide when the microscope slide is disposed over the liquid-applying station, the improvement which comprises control means for interrupting the advance of said microscope slide along said track while the slide is in position over the liquid-applying station and resuming the advance of the slide along said track after a predetermined period of time following application of liquid to the slide.

2. The apparatus of claim 1 in which the means for advancing said microscope slide are helical conveyor elements located on opposite sides of said platen.

3. The apparatus of claim 1 in which the means for advancing said microscope slide are link chain members located on opposite sides of said platen.

4. The apparatus of claim 1 in which a motor to drive the means for advancing the microscope slide and the control means is a timer mechanism which periodically interrupts movement of the motor for a predetermined period of time.

5. The apparatus of claim 1 in which the treating liquid is supplied while the microscope slide is substantially stationary.

6. The apparatus of claim 1 in which the treating liquid is supplied prior to the interruption of the advance of the microscope slide, which interruption occurs when the slide is over the liquid-applying station.

* * * * *